United States Patent [19]
Kiefer et al.

[11] Patent Number: 5,928,627
[45] Date of Patent: Jul. 27, 1999

[54] FLUORESCENT CHELATES AS VISUAL TISSUE SPECIFIC IMAGING AGENTS

[75] Inventors: Garry E. Kiefer, Lake Jackson; Darryl J. Bornhop, Lubbock, both of Tex.

[73] Assignee: The Dow Chemical Company, Midland, Mich.

[21] Appl. No.: 08/841,959

[22] Filed: Apr. 8, 1997

Related U.S. Application Data

[63] Continuation-in-part of application No. 08/728,339, Oct. 9, 1996, abandoned, which is a continuation-in-part of application No. 08/635,142, Apr. 19, 1996, abandoned.

[51] Int. Cl.$^6$ .................................................. A61K 49/00
[52] U.S. Cl. .......................................... 424/9.6; 424/9.61
[58] Field of Search ...................... 424/9.6, 9.61, 424/1.65, 9.36, 9.361, 9.362, 9.363; 534/10, 15, 16; 514/80, 286, 293; 530/386; 540/465, 472

[56] References Cited

U.S. PATENT DOCUMENTS

| | | |
|---|---|---|
| 4,920,195 | 4/1990 | Kankare et al. . |
| 4,976,950 | 12/1990 | Simon et al. . |
| 5,312,922 | 5/1994 | Diamandis . |
| 5,385,893 | 1/1995 | Kiefer et al. ............................ 514/80 |
| 5,457,186 | 10/1995 | Mukkala et al. ........................ 534/15 |
| 5,507,287 | 4/1996 | Palcic et al. . |
| 5,645,818 | 7/1997 | Jackels et al. ...................... 424/9.363 |

FOREIGN PATENT DOCUMENTS

| | | |
|---|---|---|
| 0 391 766 | 10/1990 | European Pat. Off. ...... C07D 471/18 |
| 95/26673 | 10/1995 | European Pat. Off. . |
| 93/11802 | 6/1993 | WIPO ............................ A61K 49/04 |
| 94/26275 | 11/1994 | WIPO ............................ A61K 31/44 |

OTHER PUBLICATIONS

E. Sonini and T. Lovgren, Crit. Rev. Anal. Chem. 18, 105–154 (1987).
G. Kallistratos, Chemlka Chronika New Series, 11, 249–266 (1982).
Sherry, Inorganic Chemistry, 26, 958–960 (1987).
American Review of Respiratory Disease, (Dec. 1992), 146(6), 1458–61. (Medline 93089659).
Analytical and Quantitative Cytology and Histology, (Feb. 1995), 17(1), 69–74. (Medline 95283668).
Chest (Mar. 1991), 99(3), 742–3. (Medline 91138403).
Lasers in Surgery and Medicine, (1991), 11(2), 99–105. (Medline 91238302).
Kim, *Inorg. Chem.* 34 2233–2243 (1995).
Chest, (Jan. 1993), 103 (1 Suppl., 12S–14S), Ref: 40. (Medline 93105689).

*Primary Examiner*—Jose' G. Dees
*Assistant Examiner*—Michael G. Hartley
*Attorney, Agent, or Firm*—Karen L. Kimble

[57] ABSTRACT

Fluorescent chelates of terbium and europium with tri- and tetra-cyclopolyazamacrocyclic compounds are discussed which can be used as fluorescent in vitro or in vivo diagnostic agents. These chelates are tissue specific imaging agents.

6 Claims, 9 Drawing Sheets

FLUORESCENT CHELATES AS VISUAL TISSUE SPECIFIC IMAGING AGENTS

CROSS REFERENCE TO RELATED APPLICATION

This is a continuation-in-part application of U.S. application Ser. No. 08/728,339, now abandoned, filed Oct. 9, 1996, which is a continuation-in-part application of U.S. application Ser. No. 08/635,142, filed Apr. 19, 1996, now abandoned.

FIELD OF THE INVENTION

This invention concerns visual, tissue specific terbium, europium, samarium or dysprosium chelates which can be used as visual contrast enhancement agents or diagnostic agents.

BACKGROUND OF THE INVENTION

Fluorescence imaging is found at the heart of numerous chemical and biomedical analysis schemes. Many of these schemes are based on the introduction of a fluorescent species as a marker, stain, dye or indicator [J-M. Devoisselle et al., *Optical Engineering* 32(2), 239 (1993); R. P. Haugland and A. Minta, "Design and Application of Indicator Dyes," *Noninvasive Techniques in Cell Biol.*, ed. B. H. Satir, Chap. 1, p 1, (Wiley-Liss, New York, N.Y., 1990); D. J. Gross, "Quantitative Single Cell Fluorescence Imaging of Indicator Dyes," *Noninvasive Techniques in Cell Biol.*, ed. B. H. Satir, Chap. 2, p 21, (Wiley-Liss, New York, N.Y., 1990)].

Organic chelates derived from lanthanide ions have become increasingly important as sensitive fluorescent markers for time resolved fluorometric assays [E. P. Diamandis, *Clin. Biochem.* 21, 139–150 (1988); *Clin. Chim. Acta.* 194, 19–50 (1990); *Anal. Chem.* 62, 11 49A–11 57A (1990); E. Soini and T. Lovgren, *Crit. Rev. Anal. Chem.* 18, 105–154 (1987)]. In particular, terbium and europium complexes are of significant value for these applications because of the efficient fluorescent emission in the visible region (E. P. Diamandis, U.S. Pat. No. 5,312,922). Both of these ions display a weak fluorescent emission in their non-complexed form, but when chelated with an appropriate organic ligand this visible emission is dramatically enhanced. Thus, the organic ligand acts as an antenna for absorbing ultraviolet radiation and transferring this energy to the metal ion which then dissipates the absorbed energy in the form of visible light. The mechanistic details of this phenomenon are well studied and have been extensively documented [A. P. B. Sinha, *Fluorescence and Laser Action in Rare Earth Chelates/Spectroscopy in Inorganic Chemistry* Volume II, Academic Press, (1971)].

There are numerous chelates capable of long-lived fluorescence but not all of these complexes are suitable for biological applications, one reason being due to their instability in aqueous media [G. Kallistratos, *Fluorescent Properties of Aromatic Complexes with Rare Earths and Other Elements of the IIIa-Group/Chemika Chronika*. New Series, 11, 249–266 (1982)]. In fact, a large majority of fluorescent chelates are operative in non-aqueous conditions only. This is largely due to the instability of the complex in aqueous solutions resulting in non-complexed metal being present and quenching of the fluorescent pathway responsible for visible light emission. Ultimately, complexes of this type would not be sensitive markers at low concentrations and would present toxicity problems in vivo because of metal deposition in soft tissue.

In recent years chelating agents based upon tetraazamacrocyclic backbones have proven to be extremely valuable for generating aqueous stable lanthanide chelates. In particular, aminocarboxylate and aminophosphonate chelating agents derived from 1,4,7,10-tetraazacyclododecane have been shown to form highly stable lanthanide chelates [W. P. Cacheris, A. D. Sherry, *Inorg. Chem.* 26, 958–960 (1987); J. Simon, J. R. Garlich, D. A. Wilson, and K. McMillan, U.S. Pat. No. 4,976,950]. The superior nature of this class of chelates has made them useful for diagnostic and therapeutic medical applications such as magnetic resonance imaging and bone marrow ablation. In addition, certain types of these macrocyclic chelating agents incorporating an aromatic moiety, such as the pyridine nucleus, have displayed very efficient fluorescent properties with terbium and europium (J. Kankare, J. Takalo, and P. Pasanen, U.S. Pat. No. 4,920,195). In this patent Kankare et al. demonstrate that a 14-member macrocyclic europium chelate containing a pyridine nucleus can be conjugated to human IgG. The resulting conjugate thus contains a highly sensitive fluorescent tag (the chelate) which can be quantified by fluorescent immunoassay procedures.

Use of paramagnetic macrocyclic chelates based upon gadolinium (Gd) as contrast agents for magnetic resonance imaging has attracted considerable attention. The appeal of the lanthanide chelates is directly attributed to their kinetic and thermodynamic stability under the challenging aqueous environment encountered in the human body. Appropriate modifications can be made to this type of ligand which will cause pronounced fluorescence when lanthanides, such as terbium (Tb) and europium (Eu), are at the central core. Kim et al., *Inorg. Chem.* 34, 2233–43 (1995), have reported a recent study on some potential MRI contrast agents based upon macrocyclic pyridine containing ligands. In this study, the inner sphere water coordination was determined by measuring the fluorescent properties of the terbium and europium chelates.

The importance of macrocyclic lanthanide chelates for medical applications has continued to grow with the development of tissue specific agents. Thus far, applications have focused on chelation of radioactive and paramagnetic metal ions for therapy and diagnosis (J. Simon, J. R. Garlich, D. A. Wilson, K. McMillan, U.S. Pat. No. 4,976,950; examples of gadolinium chelates for MRI are Prohance™ by Squibb and Dotarem™ by Guerbet). However, these chelates do not have any fluorescent properties.

Thus far, commercial applications of fluorescent chelates have been restricted primarily do to the labeling of proteins and antibodies for immunoassays [E. P. Diamandis, *Clinica Chimica Acta* 194, 19–50 (1990); U.S. Pat. No. 5,312,922]. Products such as FIAgen™ (CyberFluor Inc., Toronto, Ontario, Canada) are available and utilize the europium chelate of 4,7-bis(chlorosulfonyl)-1,10-phenanthroline-2,9-dicarboxylic acid as the fluorescent label. Fluorescent labels of this type are extremely sensitive and can be detected in the subpicomolar range using time resolved fluorometry.

One of the most important features of diagnostic and therapeutic agents is that they must enhance the accuracy of assessing and treating a disease state. Most frequently this involves delivering the diagnostic agent to a specific organ or soft tissue where a suspected abnormality may be present. Currently, the covalent attachment of a small molecule (i.e., diagnostic or therapeutic fragment) to a large protein or antibody is receiving much attention as the method of choice for achieving tissue specificity. However, this method is inherently complex and expensive since it involves the use of a specialized antibody which must be attached to the active agent.

Therefore, it would be advantageous to use a small molecule diagnostic agent which would localize in a specific tissue of the body without the need for attachment to a delivery molecule such as an antibody. Furthermore, if a stable, fluorescent lanthanide chelate were to exhibit tissue specificity, it would be possible to visually determine the presence of the chelate by illuminating with the appropriate light source. Potential applications would be fluorescent guided surgical procedures, in vivo imaging of bone cell growth or morphology, and examinations of the gastrointestinal tract.

SUMMARY OF THE INVENTION

Figure 1:
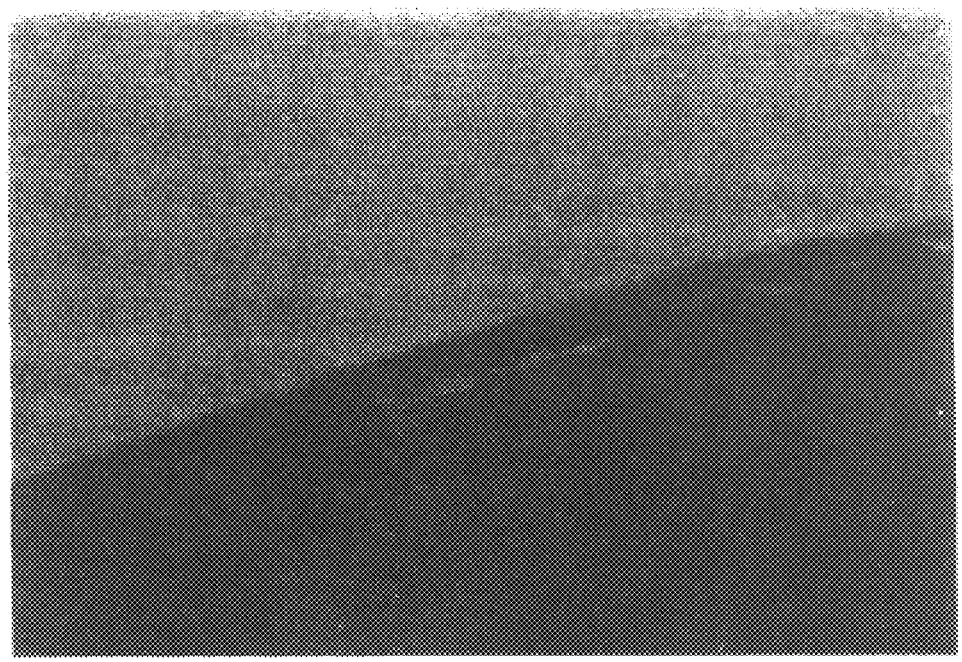
FIG. 1, a photograph, shows a cross section of a rat colon with Tb-PCTMB at about 0.01 mmol/Kg.

The present invention is directed toward novel tissue specific terbium or europium chelates which can be used as visual diagnostic agents. In particular, the preferred chelates are constructed from polyazamacrocyclic compounds of Formula I which contain a pyridine nucleus as either a part of the macrocyclic backbone or as a pendant ligating moiety.

The present invention is directed to novel complexes that are tri- and tetra-cyclopolyazamacrocyclic compounds, and derivatives thereof, of the formula (I)

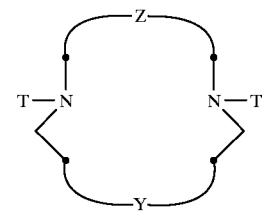

wherein:

Z is

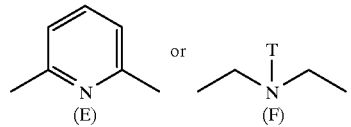

Y is

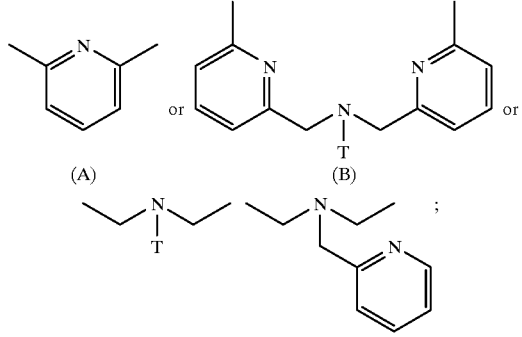

T is —CH$_2$—COOH,

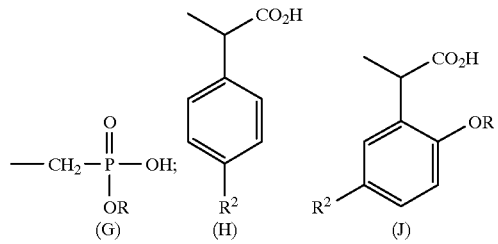

where: R is H, C$_1$–C$_4$ alkyl or —CH$_2$CF$_3$;

R$^2$ is a NO$_2$, NH$_2$, isothiocyanato, semicarbazido, thiosemicarbazido, maleimido, bromoacetamido or carboxyl group;

with the proviso that Z is only (F) when (D) is present and Z is only (E) when (A), (B) or (C) is present;

with the proviso that when T is (H) or (J), then only one (H) or (J) may be present;

complexed with a metal ion of terbium (Tb), europium (Eu), samarium (Sm) or dysprosium (Dy); or pharmaceutically-acceptable salts thereof.

Conventional pharmaceutical solutions of the chelates are used in preparing pharmaceutical formulations for injection or to bath or wash the desired area.

Biodistribution studies performed on Sprague Dawley rats indicate tissue selectivity. Fluorescence images of bone and intestinal tissues are presented and demonstrate the potential for using the lanthanide chelates to perform site-directed in vivo imaging. It is also possible to prepare the bifunctional ligand or chelate for one T and then prepare its conjugate to a biologically active material. The chelate [Formula (I) where one T is (H) or (J)] may be used for in vitro immunoassay or DNA hybridization of tissue samples (e.g., blood, plasma, cell samples) where an effective amount of the chelate is placed with the sample and then the results are read.

DETAILED DESCRIPTION OF THE INVENTION

The accuracy of early stage spectroscopic imaging in soft tissue can be enhanced significantly through the use of site directed molecules (contrast agents) which concentrate in a specific tissue.

The use of terbium (Tb) or europium (Eu) as the central metal ion to render a tissue specific fluorescent probe is very appealing. Derivatives of this type would be valuable for visual assessment of tissue conditions such as early detection of cancer and would not depend upon protein conjugation to reach their target. Furthermore, concentration of the active fluorescent material could conceivably be much higher than in the case of immunoassays making detection much easier. The present complexes have an excitation band of 250 to 290 nm and a spike emission with peaks at bands of 490 to 510 nm, 540 to 560 nm, 590 to 600 nm and 615 to 635 nm, high quantum efficiency and millisecond relaxation lifetimes which allow signal collection after prompt tissue autofluorescence has subsided and allows data collection outside the range for normal tissue fluorescence. In contrast to other fluorescent chelates which are readily quenched in aqueous media, the visual fluorescence does not degenerate in water, making them well suited for animal in vivo imaging applications. Furthermore, chelates derived from this family of macrocyclic ligands are among the most thermodynamically and kinetically inert lanthanide complexes, a paramount consideration for biological studies where metal ion toxicity is of major importance.

The terms used in Formula (I) and for this invention are further defined as follows. "$C_1$–$C_4$ alkyl", include both straight and branched chain alkyl groups. An "animal" includes a warm-blooded mammal, preferably a human being. As used herein, "complex" refers to a complex of the compound of the invention, e.g. Formula (I), complexed with a metal ion, where at least one metal atom is chelated or sequestered.

"Biologically active material" refers to a dextran, peptide, or molecules that have specific affinity for a receptor, or preferably antibodies or antibody fragments.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate", the "antibody" is meant to include whole antibodies and/or antibody fragments, including semisynthetic or genetically engineered variants thereof. Such antibodies normally have a highly specific reactivity. Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Possible antibodies are 1116-NS-19-9 (anti-colorectal carcinoma), 1116-NS-3d (anti-CEA), 703D4 (anti-human lung cancer), 704A1 (anti-human lung cancer) and B72.3. The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

The bifunctional chelating agents described herein (represented by Formula I) can be used to chelate or sequester the metal ions so as to form metal ion chelates (also referred to herein as "complexes" or "bifunctional chelates"). The complexes, because of the presence of the functionalizing moiety (represented by $R^2$ in Formula I), can be covalently attached to biologically active materials, such as dextran, molecules that have specific affinity for a receptor, or preferably covalently attached to antibodies or antibody fragments. Thus the complexes described herein may be covalently attached to an antibody or antibody fragment or have specific affinity for a receptor and are referred to herein as "conjugates".

As used herein, "pharmaceutically-acceptable salts" means any salt or mixtures of salts of a compound of Formula (I) which is sufficiently non-toxic to be useful in diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic acid, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the compounds of Formula (I) where the salt is potassium, sodium, or ammonium. Also included are mixtures of the above salts.

Of course, the free acid of the compounds of formula (I) may be used, also the protonated form of the compounds, for example when the carboxylate is protonated and/or the nitrogen atoms, i.e. when the HCl salt is formed.

Methods of Making

The complexes are prepared by methods well known in the art. Thus, for example, see Chelating Agents and Metal Chelates, Dwyer & Mellor, Academic Press (1964), Chapter 7. See also methods for making amino acids in *Synthetic Production and Utilization of Amino Acids*, (edited by Kameko, et al.) John Wiley & Sons (1974). An example of the preparation of a complex involves reacting a bicyclopolyazamacrocyclophosphonic acid with the metal ion under aqueous conditions at a pH from 5 to 7. The complex formed results in a stable nuclide composition, e.g. stable to the disassociation of the nuclide from the ligand.

The following Schemes 1–3 provide a detailed discussion of the preparation of the complexes of this invention.

Scheme 1

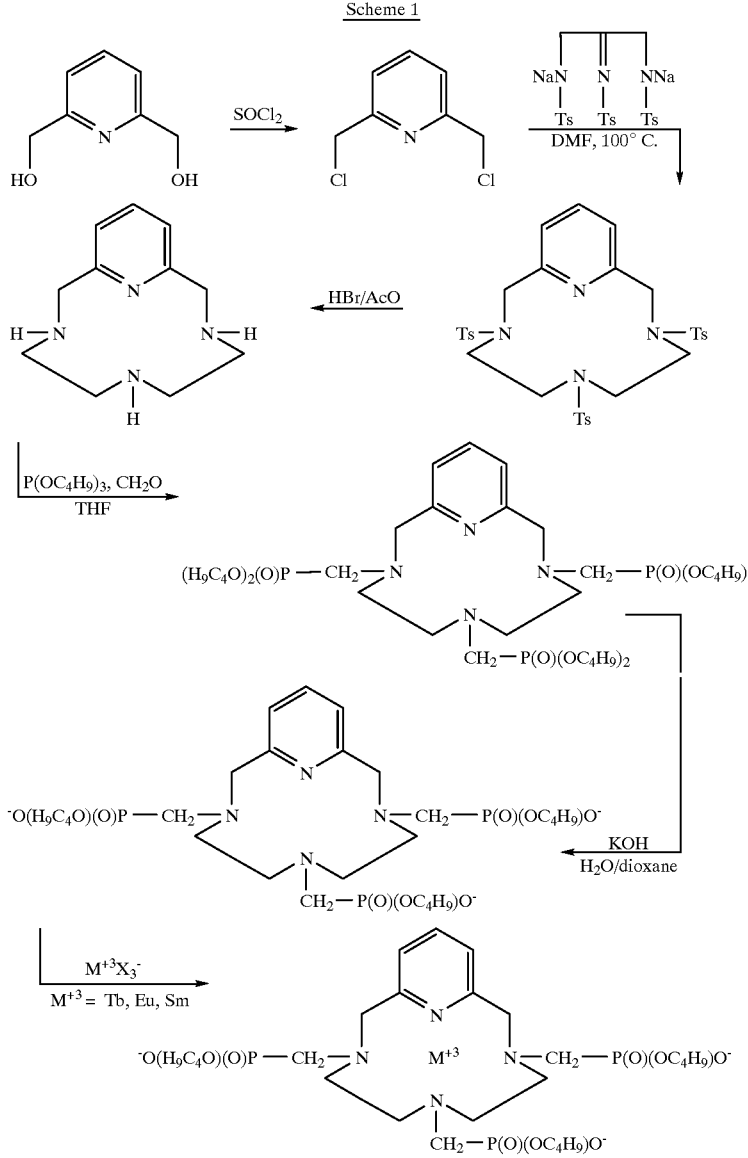

Scheme 1 shows the synthesis for preparing the 12-membered tetraazamacrocyclic structure possessing one pyridine moiety. 2,6-Bis(hydroxymethyl)pyridine is first converted to the chloromethyl derivative. In a separate step, diethylene tetraamine is tosylated and converted to the sodium salt. These two reagents are then combined in DMF to give the N-tosylated macrocycle. Deprotection of the amines is then accomplished by heating in a mixture of acetic acid (AcOH) and HBr. The N-alkyl phosphonate esters are then synthesized by reacting the secondary amines of the macrocycle with a trialkyl phosphite and paraformaldehyde in tetrahydrofuran (THF). The resulting phosphonate ester is then selectively hydrolyzed under basic conditions to give the monoalkyl phosphonate which gives the desired fluorescent chelate when treated with the chloride of Tb, Eu, Sm or Dy.

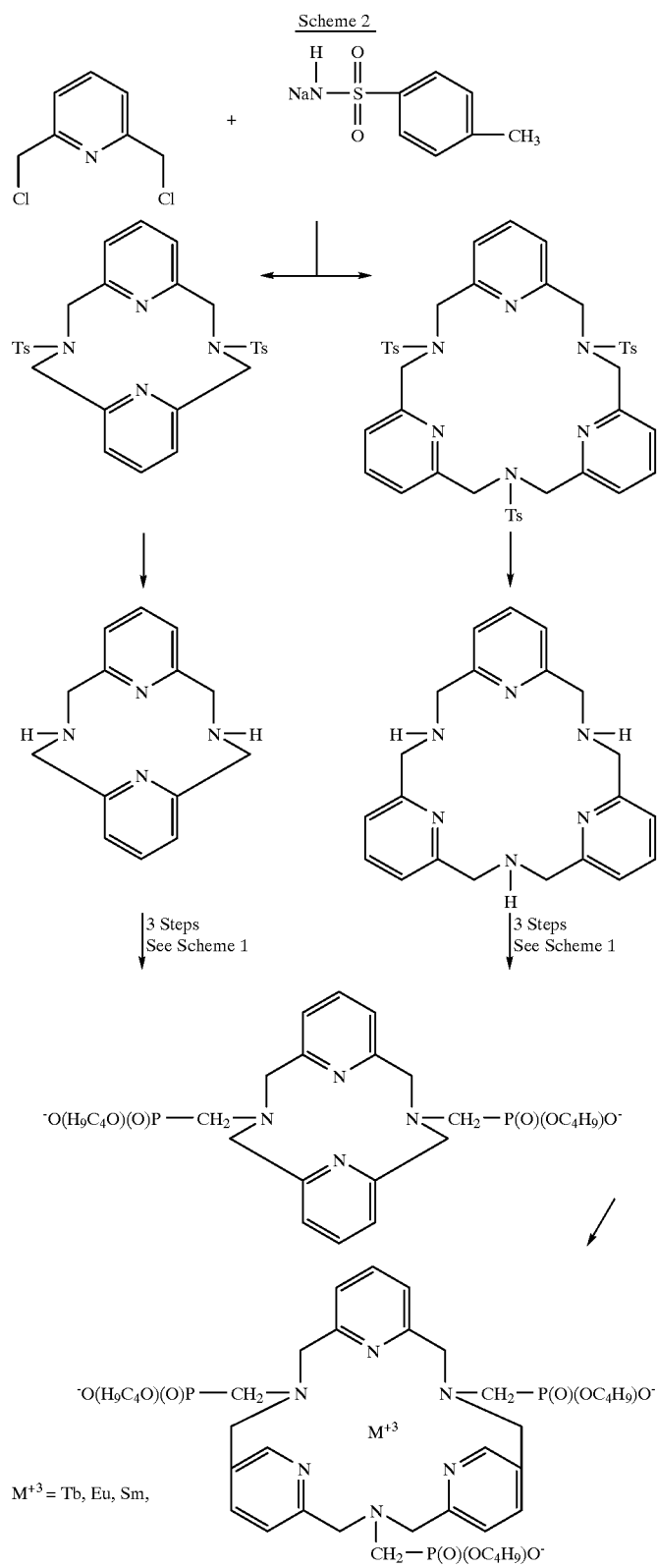
Scheme 2 outlines the synthesis of the macrocyclic structures possessing two and three pyridine moieties in the backbone. These basic structures are generated by the treatment of bis(chloromethyl)pyridine with toluenesulfonamide. This single reaction produces both the 12 and 18-membered macrocycles which are easily separated. Subsequent reactions to produce the fluorescent chelates are identical to those steps outlined in Scheme 1.

Scheme 3

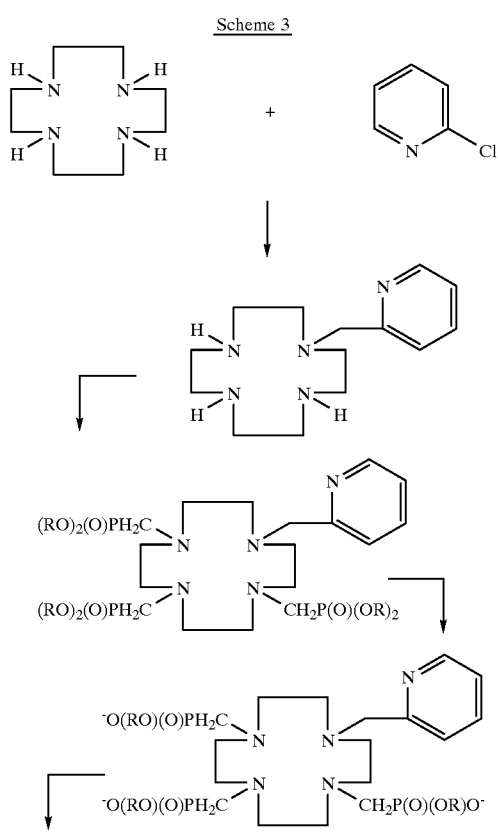

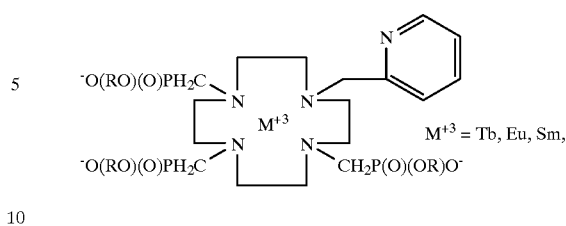

$M^{+3}$ = Tb, Eu, Sm,

Scheme 3 describes the synthesis of the 12-membered tetraazamacrocycle possessing a pyridyl pendant moiety attached at one of the secondary nitrogen positions. Covalent attachment of the pyridyl moiety is accomplished by reacting 1,4,7,10-tetraazacyclododecane with 2-chloromethyl pyridine in an aprotic solvent such as DMF. Conversion to the desired ligand and subsequent chelate is conducted as outlined in Scheme 1.

The complexes of the present invention are administered at a ligand to metal molar ratio of at least about 1:1, preferably from 1:1 to 3:1, more preferably from 1:1 to 1.5:1. A large excess of ligand is undesirable since uncomplexed ligand may be toxic to the animal or may result in cardiac arrest or hypocalcemic convulsions.

The bifunctional compounds of this invention are prepared as shown in Scheme 4.

Scheme 4

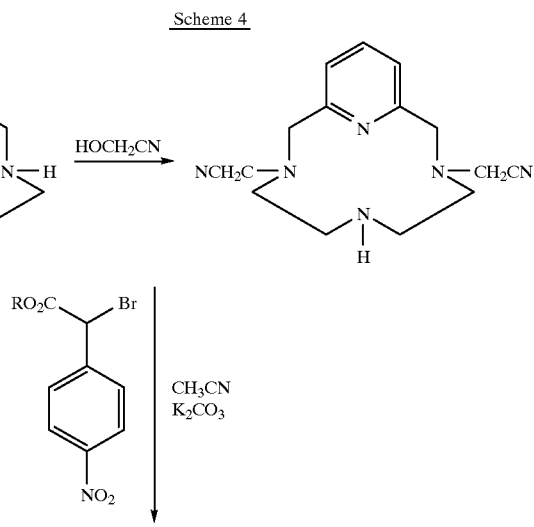

-continued

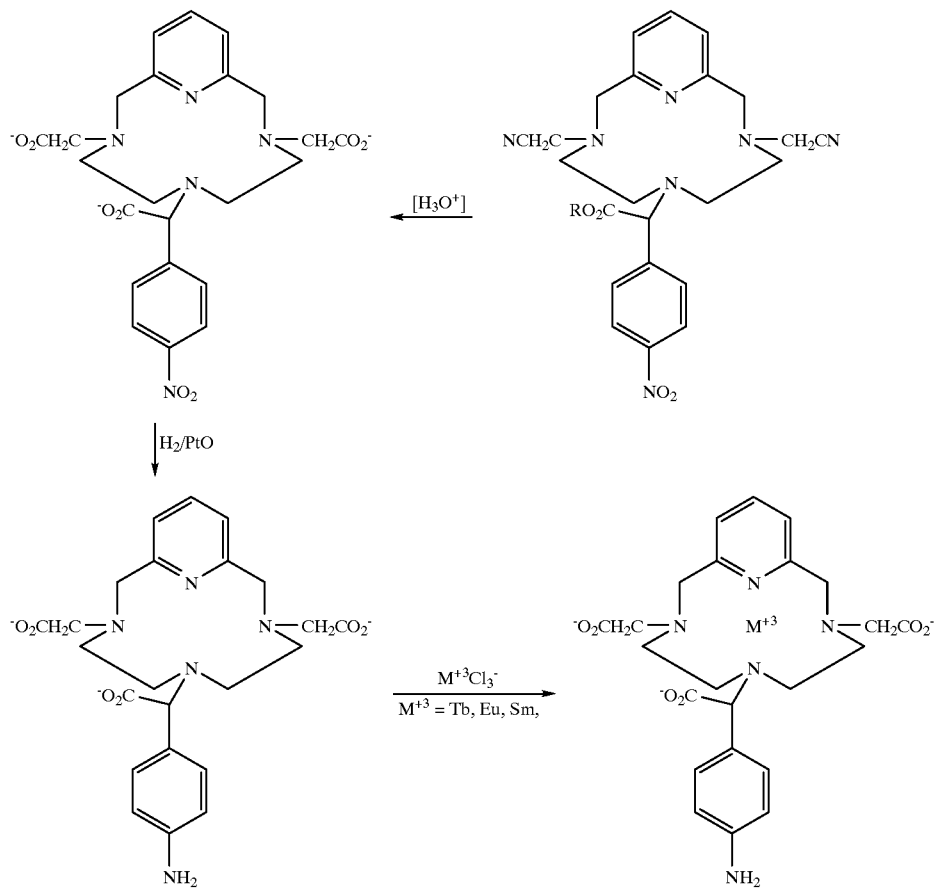

Scheme 4 outlines the synthesis of a bifunctional chelate which can be covalently attached to a biologically active material such as a monoclonal antibody. 3,6,9,15-Tetraazabicyclo[9.3.1]pentadeca-1(15),11,13-triene (PYCLEN) is reacted with glycolonitrile at a pH between 5–7. The resulting 3,9-bis-substituted nitrile is then further alkylated at the 6-position using bromo(4-nitrophenyl) methyl acetate. The resulting product is then hydrolyzed under acidic or basic conditions transforming the two nitriles and the ester functionalized to aminocarboxylic acids. The aromatic nitro substituent is then reduced using hydrogen and platinum oxide ($H_2$/$PtO_2$) to an aniline functionality. This Scheme 4 can be use for any compound of Formula I where one T is (H) or (J). The resulting ligand can then be chelated with a fluorescent lanthanide and conjugated to a biologically active material by established procedures.

Preferred features of the compounds of Formula I are those where: T at least one T is —$CH_2P(O)(OH)(OR)$ and one T is an (H) or (J) moiety.

Starting Materials

The ligands of Formula (IA) and (IB) are known from our U.S. Pat. No. 5,385,893, issued Jan. 31, 1995, the disclosure of which is hereby incorporated by reference. Another published equivalent is WO 94/26726, published on Nov. 24, 1994.

The ligands of Formula (IC) are known from our copending U.S. patent application Ser. No. 08/058,101, filed May 6, 1993, the disclosure of which is hereby incorporated by reference. Another published equivalent is WO 93/11802, published on Jun. 24, 1993.

The ligands of Formula (ID) are known from our U.S. Pat. No. 5,462,725, issued Oct. 31, 1995, the disclosure of which is hereby incorporated by reference. Another published equivalent is WO 94/26275, published on Nov. 24, 1994.

"Complex" and "chelate" are used to mean a metal ion with a ligand as shown in Formula (I).

"Bifunctional chelate" refers to a complex or chelate where one T of Formula (I) is (H) or (J).

$TbCl_3$ and $EuCl_3$ were purchased from Aldrich Chemical.

Utility

The complexes, bifunctional chelates and conjugates of the present invention are useful as diagnostic agents in the manner described. These formulations may be in kit form such that the two components (i.e., ligand and metal, complex and antibody, or ligand/antibody and metal) are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethylene oxide adducts, napthalenesulfonates, alkylbenzenesulfonates, and the polyoxyethylene sorbitan esters.

For injectable applications the active chelate is given at a dose of about 0.001 to about 0.2 mmol/kg. For applications where a tissue is rinsed with the fluorescent chelate prior to examination, the chelate solution can vary in concentration depending upon the specific requirements.

The complexes so formed can be attached (covalently bonded) to an antibody or fragment thereof and used for therapeutic and/or diagnostic purposes. The complexes and/or conjugates can be formulated for in vivo or in vitro uses. A preferred use of the formulated conjugates is the diagnosis of diseased states (e.g., cancer) in animals, especially humans.

This invention is used with a physiologically acceptable carrier, excipient or vehicle therefore. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis. The dose will vary depending on the disease and physical parameters of the animal, such as weight. In vivo diagnostics are also contemplated using formulations of this invention.

Methods of Using

Tissue specificity may also be realized by ionic or covalent attachment of the chelate to a naturally occurring or synthetic molecule (e.g. through T which contains one (H) or (J) where $R^2$ is a $NO_2$, $NH_2$, isothiocyanato, semicarbazido, thiosemicarbazido, maleimido, bromoacetamido or carboxyl group) having specificity for a desired target tissue. One possible application of this approach is through the use of chelate conjugated monoclonal antibodies which would transport the chelate to diseased tissue enabling visualization. The surgeon could then illuminate soft tissue with a UV light source coupled with an appropriate detector, if necessary, and surgically remove the indicated tissue.

Figure 5:
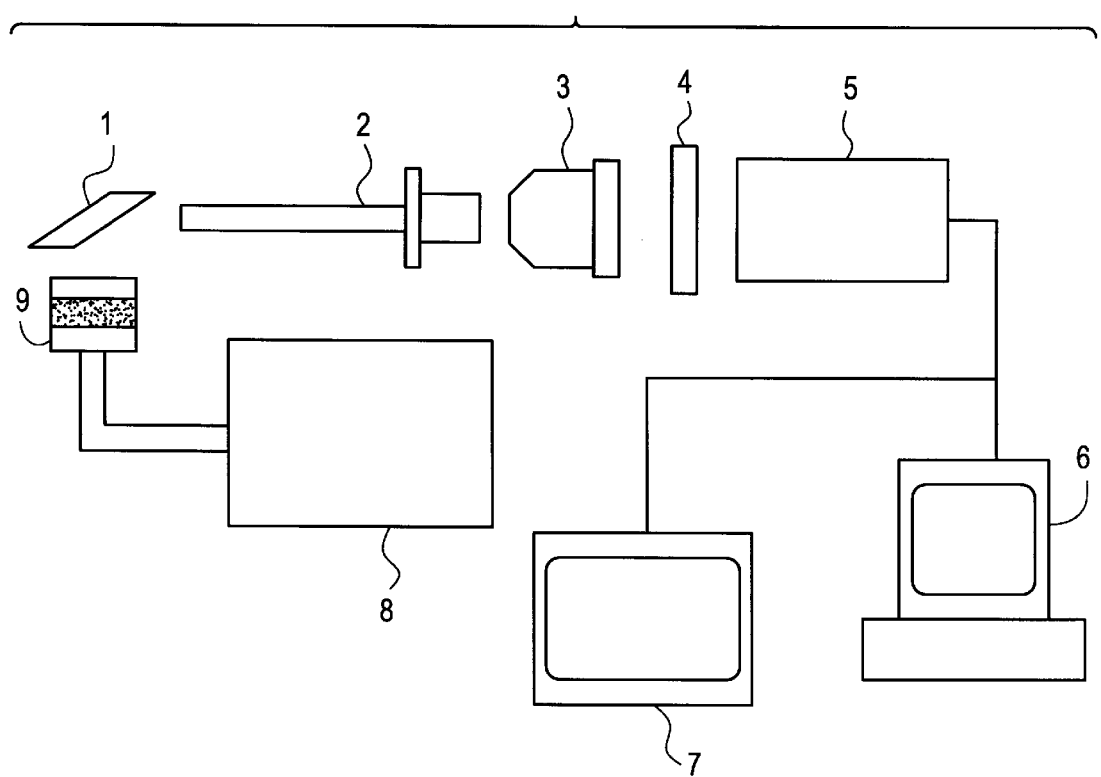
FIG. 5 is the block diagram of the micro-endoscope fluorimeter used with complexes of this invention.

The complexes or bifunctional chelates formed with the compounds of Formula I of this invention are imaged using a method for detection of the emission which combines microscopic interface with remote imaging technology to allow in vivo images. One suitable apparatus is shown in FIG. 5. The target sample (1) is placed on or viewed through a resolution target that has groups of lines and elements that are a made from a black emulsion deposited onto a white positive background (clear glass). Images are obtained by back or front illuminating the target with a source (8), such as an IR filtered xenon discharge lamp or liquid light guide with a 150 watt UV light source. The color of light is electronically controlled. Rapid response is possible and easy shifting between the fluorescence and white light images is possible. The beam from the optical fiber passes through a diffuser having in-house construction or through a 270 nm interference filter (9) having a 10 nm band width. The distance between the scope tip (left end of (2)) and the target (1) is chosen for the best in-focus image. The image is collected by a endoscopic fluorescence imaging microscope (2) which may contain a flexible or ridged imaging transfer device made of either quartz fiber bundles or thin rod lens. A fiber optic fluorescence imaging microscope is flexible; the rod lens fluorescence imaging microscope is ridged but has better light through put. The best resolution used for this invention had a fiber optic conduit having 10,000 pixels, each measuring 3 $\mu$m in diameter. The best commercial fluorescence imaging microscope available would be preferable to use which have greater than 20,000 pixels, each measuring 3 $\mu$m in diameter. The image may be collected at different viewing angles with respect to the central viewing axis of the thin rod lens endoscope. A 10× microscope objective (3) is placed 10 mm from the scope (2), which collects, magnifies and plays the image onto a charge coupled device (CCD, (5)) which may be thermoelectricity cooled. An interference filter (4) is present between the microscope objective (3) and the CCD (5), such as a 520 nm or 550 nm filter, when the fluorescence image is obtained. Examples of these interference filters are two position filter wheel (where no filter is present for white light), a liquid crystal filter (which is very specific, Cambridge Research Instrument), or a monochrometer. The image collected by the CCD is displayed on a high resolution video monitor (7) which provides the image for visual display in real time, grabbed by a frame grabber and down loaded to a PC (6) for image processing and analysis or recorded onto a video cassette (VCR) for subsequent digitization. A camera control unit (CCU) could be present between the monitor (7) and the PC (6). The software produces a graph of light intensity as a function of position across the line pairs. This digitized image provides a grey scale image. The limiting resolution (LP/mm) is calculated using an aerial image modulation (AIM) plot. This method facilitates the non-invasive quantitation of the transport process under constant light intensity and at a fixed magnification. This is the preferred method used with the complexes of this invention.

Other methods are also known which could also be used, such as the endoscopic imaging system described in U.S. Pat. No. 5,507,287.

THEORY OF THE INVENTION

While not wishing to be bound by theory, it is believed that the advantageous results of the present invention are obtained because common to all chelates of this invention, the cation is positioned at an apical position above the 12-membered macrocycle and held in place through an ionic interaction with a phosphonic acid ligating group. It is this unique combination of functionalized nitrogen positions and ligating groups within the macrocyclic framework which enables chemical modifications leading to tissue selectivity.

The fluorescence of lanthanide salts such as Tb and Eu in aqueous solution is very weak because the ions do not efficiently absorb the necessary energy. However, the fluorescence of these ions can be dramatically enhanced when the metal is complexed with an appropriate organic ligand.

In this unique complex, the ligand absorbs UV radiation and is excited from the ground state ($S_0$) to an excited state ($S_1$). As the ligand begins to return to its initial ground state, some of the energy is transferred from the triplet state of the ligand to an appropriate 4 f energy level of the lanthanide ion. When receiving energy from the triplet state of the ligand, the ion comes to the resonance state and can undergo a radiative transition resulting in the characteristic line emission of the metal ion (ion fluorescence). In these chelate structures the ligand essentially acts as an antenna for absorbing energy which is transferred to the metal ion and reemitted in the form of visible light. It is also advantageous to have a ligand which absorbs energy at a significantly different wavelength than what is emitted by the metal ion to minimize interference (Stoke's shift).

There have been numerous fluorescent chelates reported. A great majority of these chelates are operative in anhydrous media only because fluorescence is quenched by water. The chelates of the present invention are far superior for biological applications because of their ability to form stable, fluorescent chelates in an aqueous environment. The unique positioning of the pyridine functionality, as either part of the macrocyclic ring or as a pendant group, enables efficient energy transfer to the metal ion and also augments overall chelate stability.

The invention will be further clarified by a consideration of the following examples, which are intended to be purely exemplary of the present invention.

Chelate Synthesis

EXAMPLE 1
Preparation of terbium 3,6,9-tris(methylene phosphonic acid)-3,6,9,15-tetraazabicyclo[9.3.1]pentadeca-1(13),11,13-triene (Tb-PCTMP)

The free acid of 3,6,9-tris(methylene phosphonic acid)-3,6,9,15-tetraazabicyclo[9.3.1]pentadeca-1(13),11,13-triene (PCTMP) (50 mg, 0.1 mmol) was initially dissolved in deionized water (1 mL) to give an aqueous solution of pH=1.3. Terbium chloride hexahydrate (38 mg, 0.1 mmol) was then dissolved in water (1 mL) and added in one portion to the ligand solution with continuous stirring (pH=1.4). Sodium hydroxide (0.1 N) was then added in 50 µL portions until a pH=5.5 was sustained. Complexation was monitored by reverse phase HPLC eluting with methanol/water (80:20). The solution was then filtered through a 0.2 µm filter and freeze-dried to give the complex as a flocculant white solid, which exhibited a brilliant green visible emission when excited with a UV lamp. The complexation was assessed by HPLC and the yield was quantitative.

EXAMPLE 2
Preparation of terbium N,N'-bis(methylene phosphonic acid)-2,11,diaza[3.3]-(2,6)pyridinophane (Tb-BP2P)

An aqueous solution (3 mL) of N,N'-bis(methylene phosphonic acid)-2,11,diaza[3,3]-(2,6)pyridinophane (BP2P) free acid (80.8 mg, 0.19 mmol) was combined with an aqueous solution (3 mL) of terbium chloride hexahydrate (85 mg, 0.23 mmol) with stirring (pH=4). Potassium hydroxide (5 N) was then added in small aliquots (20 µL) until the solution was basic (pH=9). After stirring for 18 hours, the solution was filtered (0.45 µm) and freeze-dried. The resulting solid was dissolved in methanol (16 mL) and filtered to remove Tb(OH)$_3$. The methanol filtrate was concentrated in vacuo to give a solid which was dissolved in water (10 mL), filtered (0.2 µm), and freeze-dried. The complex was isolated as a flocculant, off-white solid. The complexation was assessed by HPLC and the yield was quantitative.

EXAMPLE 3
Preparation of europium 3,6,9-tris(methylene phosphonic acid n-butyl ester)-3,6,9,15,tetraazabicyclo[9.3.1]pentadeca-1(15),11,13-triene (Eu-PCTMB)

The potassium salt of PCTMB (150 mg, 0.19 mmol) was dissolved in deionized water (3 mL) to give a solution of pH 10.5. The pH was lowered to 5.5 using 1N HCl with continuous stirring. An aqueous solution (3 mL) of europium chloride hexahydrate (85.5 mg, 0.23 mmol) was then added in one portion to give a solution having a pH of 3.47. The pH was slowly raised by adding 0.1 mL aliquots of 0.1 N KOH. Addition of KOH was terminated when a pH of 6.4 was sustained. At this point the homogeneous solution became soapy and considerable turbidity was observed. The turbid solution was then freeze dried and the resulting solid dissolved in chloroform:methanol (3:1, 40 mL). This organic solution was filtered through Celite™ and concentrated to give a glassy solid. The solid was redissolved in water (20 mL), filtered through a 0.2µ filter and freeze dried to give the complex as a flaky, snow white solid. The complex was isolated as a flocculent, off-white solid. The complexation was assessed by HPLC and the yield was quantitative.

EXAMPLE 4
Preparation of terbium 3,6,9-tris(methylene phosphonic acid n-butyl ester)-3,6,9,15, tetraazabicyclo[9.3.1]pentadeca-1(15),11,13-triene (Tb-PCTMB)

The potassium salt of PCTMB (150 mg, 0.19 mmol) was dissolved in deionized water (3 mL) to give a solution of pH 10.5. The pH was lowered to 5.5 using 1N HCl with continuous stirring. An aqueous solution (3 mL) of terbium chloride hexahydrate (85.5 mg, 0.23 mmol) was then added in one portion to give a solution having a pH of 3.47. The pH was slowly raised by adding 0.1 mL aliquots of 0.1N KOH. Addition of KOH was terminated when a pH of 6.4 was sustained. At this point the homogeneous solution became soapy and considerable turbidity was observed. The turbid solution was then freeze dried and the resulting solid dissolved in chloroform:methanol (3:1, 40 mL). This organic solution was filtered through Celite™ and concentrated to give a glassy solid. The solid was redissolved in water (20 mL), filtered through a 0.2µ filter and freeze dried to give the complex as a flaky, snow white solid. The complex was isolated as a flocculant, off-white solid. The complexation was assessed by HPLC and the yield was quantitative.

EXAMPLE 5
Preparation of dyspersium or samarium 3,6,9-tris(methylene phosphonic acid n-butyl ester)-3,6,9,15, tetraaza-bicyclo[9.3.1]pentadeca-1(15),11,13-triene (Dy-PCTMB or Sm-PCTMB)

When the procedure of Example 4 was repeated, using the appropriate metal chloride, the corresponding chelate was obtained.

Biodistribution Studies

The details of the tissue biodistribution studies are as follows. A $^{153}$SmCl$_3$ solution was prepared as were the appropriate ligand solutions. The two solutions were thoroughly mixed at a pH=2 and the pH of the solution was raised to 7 using 0.1 N NaOH to facilitate complexation. Complexation was then evaluated by passing the sample solution (100 µL) through a Sephadex™ C-25 column eluting (2×3 mL) with 4:1 saline (0.85% NaCl/NH$_4$H) and comparing the amount of radioactivity in the eluent with that remaining on the column (free metal remains on the column). The in vivo distribution of the radioactive complexes was measured using three Sprague Dawley rats (180–220 g), each injected with 100 µL (pH 7.5) of the radioactive complex solution. After 30 minutes or 2 hours, the animals were sacrificed. The organs were removed, weighed and counted. The total percentage of the dose in bone was calculated using the standard assumptions regarding the total body weight percentages. For example, the bone sample (femur) represents 1/25 the weight of the total skeletal system and total muscle dose was calculated by assuming that muscle comprises 43% of the total body weight.

Imaging

EXAMPLE I

Figure 3:
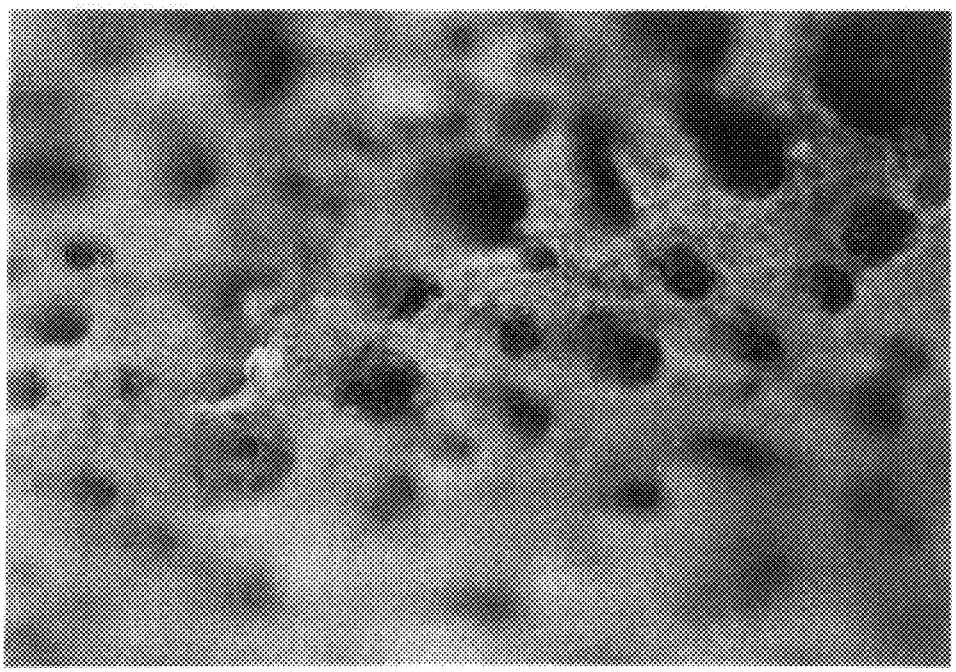
FIG. 3, a photograph, shows a 10× magnification of bone of a rat with Tb-BP2P at about 100 μL of a 1×10$^{-4}$ M solution.
Figure 4:
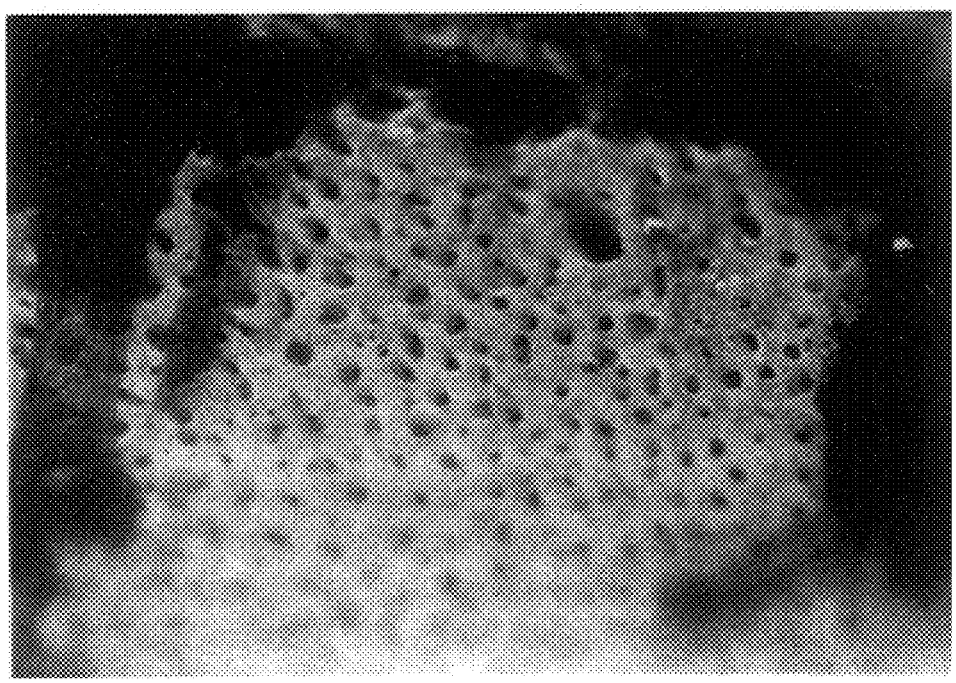
FIG. 4, a photograph, shows a 4× magnification of bone of a rat with Tb-BP2P at about 100 μL of a 1×10$^{-4}$ M solution.

Sprague Dawley rats (180–220 g) were injected with the respective Tb chelates at 0.1 mmol/Kg dose level. The animals were sacrificed and the organs removed for spectroscopic examination. Photographs were then taken using a microscope by illuminating tissue samples containing the Tb chelate with a 254 nm hand-held UV lamp equipped with a visible filter. FIGS. 3 and 4 show regions of the rat femur where high concentrations of the chelant are present as evidenced by intense green emission. FIG. 3 and show as the chelate Tb-BP2P. The distribution of the chelate appears to be fairly uniform and can be detected in porous regions of the bone where capillary blood supply is abundant. Emission appears to be more intense at end-bone regions which would be consistent with fast growing tissue in young animals.

Figure 2:
FIG. 2, a photograph, shows a 4× magnification of a flat view of the interior of a rat colon with Tb-PCTMB at about 0.01 mmol/Kg.

These complexes display dramatic tissue selectivity in addition to unique spectroscopy properties. Anionic Tb-PCTMP and Tb-BP2P show skeletal system uptake; neutral Tb-PCTMB shows substantial lipophilic character. Tb-PCTMB enhances interactions between the chelate and blood proteins resulting in substantial hepatobiliary uptake. Since the rat has no gall bladder, the chelate is transported directly to the gastrointestinal tract. Thus, Tb-PCTMB concentrates in the small intestine, Tb-BP2P resides primarily in the bone. FIGS. 1 and 2 show these results for Tb-PCTMB.

Based on these results, it appears possible that these chelants can be used to detect abnormalities as seen in animals such as humans with diseases such as osteoporosis and as they are soluble in blood and other aqueous media can also be used for fluid movement in biological matrices.

EXAMPLE II

The quantitative, multi-dimensional, remote, micro-endoscopic imaging of rat small intestine in vivo was performed using Tb-PCTMB (prepared in Example 1). The optical train allows spatial imaging on the micron level and sensitivity at the picogram level.

A block diagram of the micro-endoscopic fluorimeter used is shown in FIG. 4. The sample was remotely illuminated through a liquid light guide with a 150 watt UV light source, coupled to a 270 nm interference filter with a 10 nm bandwidth. Fluorescent images were collected with a 210 nm Hopkins thin-rod lens. The image from the scope is passed through a 550 nm interference filter with a 10 nm bandwidth and then played onto a thermoelectricity cooled CCD. The CCD signal is displayed on a personal computer and frames are grabbed with accompanying control software for the camera. Quantitative image analysis is done using appropriate software. This complete apparatus optical train has a field of view of 415 mm$^2$ with resolution on the order of 181 LP/mm.

Instrument calibration is accomplished by infusing a known quantity of TB-PCTMB into a highly reflective, fibrous, solid matrix that has morphology similar to that of the tissue to be studied. The calibration standards and the tissue sample are mounted in the same position relative to the scope. The standards are prepared on six analytical grade filter paper disks, 5 mm in diameter. Aqueous solutions of Tb-PCTMB were prepared with the following concentrations: $3 \times 10^{-6}$M, $4 \times 10^{-6}$ M, $5 \times 10^{-6}$ M, $6 \times 10^{-6}$ M, $7 \times 10^{-6}$ M and $8 \times 10^{-6}$ M. To separate disks 5 $\mu$L of each of the Tb-PCTMB solutions are applied. Once dry each of the disks have 15, 20, 25, 30, 35 and 40 pmole, respectively, of Tb-PCTMB infused within. The standard disks are placed in the sample holder, excited with 270 nm light and interrogated for fluorescence at various CCD integration times (3 to 6 seconds). The fluorescence signal from each of the disks is plotted against the number of moles of Tb-PCTMB and camera integration time. These plots generate calibration curves of moles vs. time and moles vs. grey scale signal.

Tissue samples containing the site marker (Tb-PCTMB) are obtained from Sprague-Dawley rats (180–220 g) injected with 100 $\mu$L of solutions of Tb-PCTMB complex (pH=7.5, $6 \times 10^{-6}$ M) in the tail vein. The injected quantity of compound is roughly equivalent to 1 mg Tb-PCTMB/kg rat body weight. After 30 minutes, the animal was euthanized and the small intestine was removed. A small intestine section, weighing 3 mg, was mounted in the sample holder with mounting wax and imaged using a CCD at various integration times. In addition to the fluorescence image collected (FIG. 5), a white light image of the intestine sample was collected (FIG. 6) using a 150 watt white light source for illumination with emission filter removed. The fluorescent image was quantified and the amount of Tb-PCTMB was determined based on the calibration plot constructed.

Quantitative Results

The tissue sample is considered homogeneous and large with respect to the penetration depth ($\delta$) of the excitation source. The sample has an absorption coefficient, scattering coefficient and scattering anisotropy ($\mu_a$, $\mu_s$ and g, respectively). This is a one-dimensional model based upon a Monte Carlo Simulation that treats flucence rate and escape function with respect to exponential attenuation of light from the source and accounts for the dependency of light transport through the surface boundary. Assumptions include that the excitation light is uniformly delivered normal to the surface and wide with respect to penetration depth and that the light distribution varies only with penetration depth. Fluence rate ($\phi$) and escape function (G) are given as follows:

$$\phi(z) = E_o[C_1 \exp(-k_1 z/\delta) - C_2 \exp(-k_2 z/\delta)] G(z) = C_3 \exp(-k3z/\delta)$$

where z is the depth of the source fluorophore and $C_1$, $C_2$, $C_3$, $k_1$, $k_2$ and $k_3$ are parameters dependent on the diffuse reflectance, $R_d$. Empirical expressions for these parameters are:

| Calculated Parameters for Evaluating the Escape Function for Fluorescence Signal | | |
|---|---|---|
| Parameter | $\eta$ tissue/$\eta$ air | Calculated Value |
| $R_d$ | $\exp(-7\delta\eta_a)$ | 0.42 |
| $C_1$ | $3.09 + 5.44R_d - 2.12\exp(-21.5R_d)$ | 5.37 |
| $k_1$ | $1 - (1 - 1/\sqrt(3))\exp(-20.1R_d)$ | 1.00 |
| $C_2$ | $2.09 - 1.47R_d - 2.12\exp(21.5R_d)$ | 1.47 |
| $k_2$ | $1.63\exp(3.40R_d)$ | 6.80 |

-continued

Calculated Parameters for Evaluating the Escape Function for Fluorescence Signal

| Parameter | $\eta$ tissue/$\eta$ air | Calculated Value |
|---|---|---|
| $C_3$ | $0.28 + 0.78R_d - 0.14\exp(-10.7R_d)$ | 0.61 |
| $k_3$ | $1 - 0.31\exp(-6.12R_d)$ | 0.98 |

The quantitative results require calibration of the micro-endoscope fluorimeter in two facets: (1) use of a grey scale to measure the fluorescent signal as a function of analyte quantity and (2) generation of temporal response curves of detector integration time as a function of signal intensity for fixed quantities of analyte. Using the standard disks infused with Tb-PCTMB to calibrate the micro-endoscope fluorimeter, a linear, quantitative relationship was established between the fluorescence signal (integrated for 4 seconds) and the moles of Tb-PCTMB: $I=4.58Q-49.0$; $r=0.994$ where Q is the quantity of Tb-PCTMB in moles and I is the fluorescence signal, which is the average grey scale value in the image. The average grey scale value correlates with the average fluorescence signal/camera pixel. The calibration sample disks were 13,000 pixels across, which was the image size of the disk. Since we are measuring average signal/pixel other adjustments were made to determine the quantity of analyte in a sample that is a size other than 13,000 pixels by generating a calibration plot of average signal/pixel (grey scale value) vs. moles of analyte/pixel.

Figure 6A:
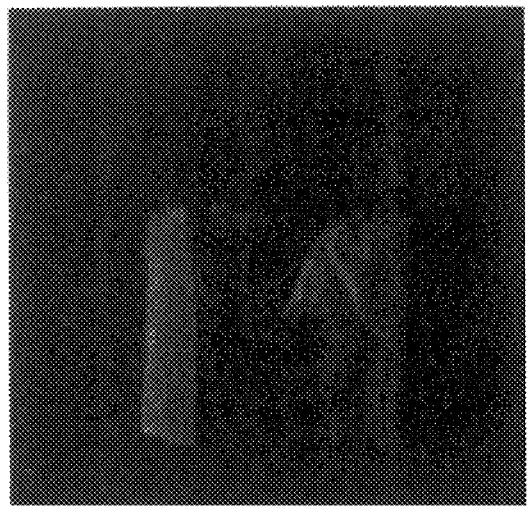
FIG. 6, a photograph, is the rat intestine image of the inner lumen using the micro-endoscope of FIG. 5 and shows the actual fluorescence image and the false color contour plot.
Figure 6B:
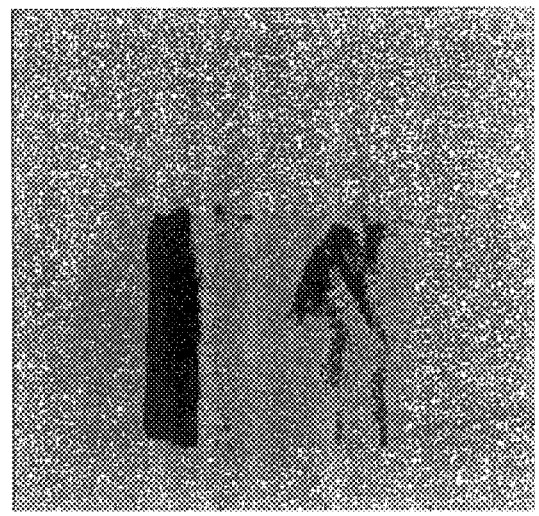
Figure 7A:
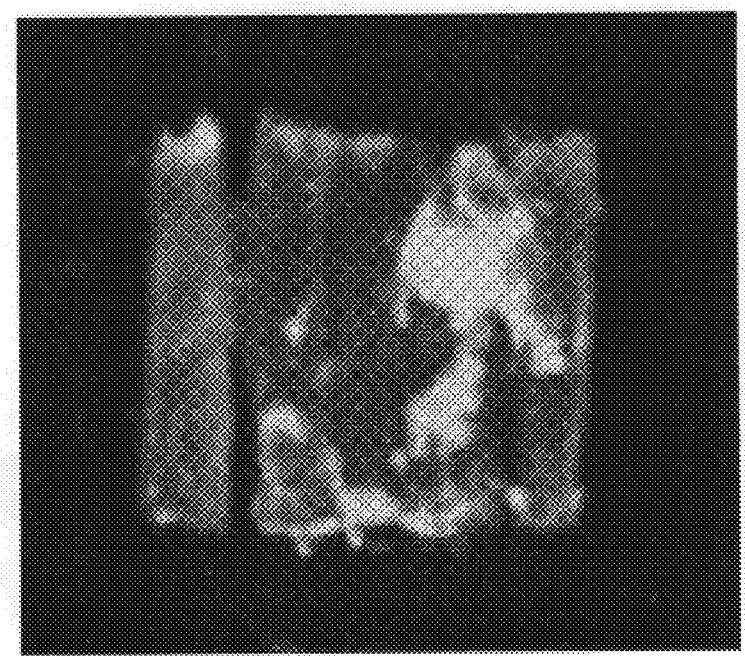
FIG. 7, a photograph, is the white light image of the same rat intestine of FIG. 6.
Figure 7B:
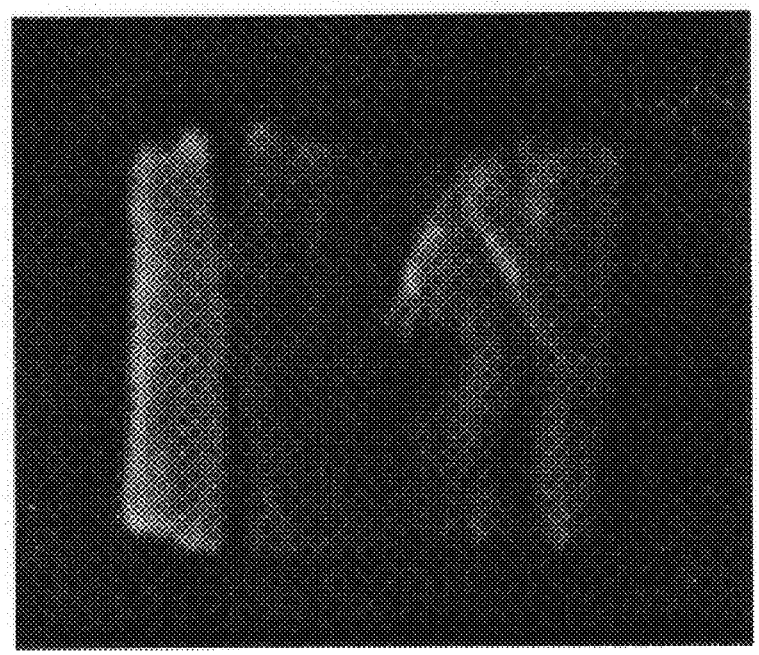

A white light image of the small intestine is shown in FIG. 7 and the corresponding fluorescence image is shown in FIG. 6. The images are grey scaled from 0 to 255 where low grey scale values correspond to dark regions in the images and large values correspond to their light regions (highly reflecting morphology). A false color plot is shown in FIG. 6 which permits the determination of the quantity of Tb-PCTMB at any point in the tissue sample by noting the color of a region of interest and finding the corresponding Tb-PCTMB quantity/pixel color scale. For example, as a first approximation the intestine of FIG. 6, false color plot, is divided into three parts which are calculated for the total quantity of Tb-PCTMB present. The results are reflected in the following table:

Results of Quantitative Calculations of Tb-PCTMB

| Sampled Region | Average Grey Scale | Sampled Pixels | Grey Scale Corrected | Total Moles of Tb-PCTMB |
|---|---|---|---|---|
| 1 | 85.66 | 1976 | 69.73 | $1.63 \times 10^{-11}$ |
| 2 | 77.18 | 228 | 62.83 | $1.43 \times 10^{-11}$ |
| 3 | 67.94 | 684 | 55.30 | $1.23 \times 10^{-11}$ |

These results demonstrate our ability to quantify the presence of a probe marker in a complex biological matrix at the picomole level.

The biodistribution data for PCTMB is shown in the table below. This data was carried out using Sprague-Dawley rats. The radioactive metal, $^{153}$Sm, is used in the complex with PCTMB. A stock solution of $^{153}$SmCl$_3$ was prepared by adding 2 mL of $3\times10^{-4}$ M of $^{153}$SmCl$_3$ in 0.1 N HCl to 2 mL of $3\times10^{-4}$ M $^{152}$SmCl$_3$ carrier solution. Appropriate ligand solution were then prepared in deionized water. After the two solutions were thoroughly mixed (pH=2), the pH was slowly raised to 7 using 0.1 N NaOH to facilitate complexation. The complexation was then evaluated by passing the sample solution (100 mL) through a Sephadex™ C-25 column eluting (2×3 mL) with 4:1 saline (0.85% NaCl/ NH$_4$OH) and comparing the amount of radioactivity in the eluent to that remaining on the column (free metal remains on the column). The rats are then injected with the complex as before, euthanized after 30 minutes, and their organs removed. Radioactive counts from the tissue yielded the quantity of chelate in each of the tissue types.

Biodistribution of $^{153}$Sm-PCTNB

| Tissue of Organ | Percent Distributed |
|---|---|
| Bone | 3.73 |
| Liver | 2.70 |
| Kidney | 0.43 |
| Spleen | 0.05 |
| Muscle | 1.09 |
| Blood | 0.14 |
| Heart | 0.02 |
| Lung | 0.04 |
| Brain | 0.00 |
| Stomach | 0.08 |
| Small Intestine | 57.98 |
| Large Intestine | 0.77 |

The sum of the value does not equal 100% because the remainder fraction passes via the excretory system or is taken up in tissues not analyzed. The 3 mg sample of tissue came from the dosed rat (0.1 mmole/kg body weight) and the total amount of analyte that resides in the small intestine is only 58% of the total quantity injected. Therefore a simple mass balance calculation is possible.

This data are written with respect to the mass of the organ analyzed, and in the small intestine the rat was injected with a quantity of 0.1 mmol probe/kg small intestine. The sample taken was 3 mg section, and using the appropriate conversion factors, about 193 picomoles of probe molecule should be in the sample. In FIG. 6 the fluorescence signal comes from approximately 23% of the total small intestine surface (meaning 44.39 picomoles should be quantified in the sample). The total quantity of the analyte found was 43.02 picomoles (3.18% error) which is encouraging given the small sample and small quantity of analyte. This detection limit shows great potential for early warning, minimally invasive diagnosis in real time.

EXAMPLE III

The optical train used is depicted in FIG. 5. For the resolution studies a 1951 USAF resolution target was used. The resolution target consists of groups of elements (lines) that are a known width, length and distance apart. The lines on the target are made from a black emulsion deposited onto a white positive background (clear glass). The images are obtained by back illuminating the resolution target using an IR filtered xenon discharge lamp. The beam from an optical fiber passes through a diffuser of in-house construction which replaces the 270 nm interference filter (4) shown in FIG. 5. The distance of the scope tip from the target (1.5 mm) was chosen so that the best in-focus image is produced. The image was collected by a 0°, 30° and 60° viewing angle with respect to the central axis of the thin rod lens endoscope. A 10x microscope objective, placed 10 mm from the endoscope, collected, magnified and played the image onto a CCD (5). The image collected by the CCD was displayed on a high resolution video monitor, grabbed by a frame grabber, and downloaded to a PC for image processing and analysis. The software produces a graph of light intensity as a function of position across the line pairs. The limiting resolution (LP/mm) is calculated using a aerial image modulation (AIM) plot and is defined as the point where the dI/dx remains constant.

Field of view measurements were made by repositioning the target so that a single line laterally spanned the field of view of the endoscope. The circular field of view is easily calculated knowing the length of the line on the resolution target the represents the diameter of the viewing zone. At the expense of image detail, the field of view can be enlarged allowing large segments of the bone to be viewed. For the fluorescent measurements, the distance between the scope and the bone sample was approximately 5 mm. The best in-focus image was found when the microscope objective is placed near its working distance and at 21 mm from the backend of the rod lens system.

Biodistribution studies were carried out as described in Example II using the corresponding $^{153}$Sm-PCTMP complex. Approximately 1 mg/kg of solute was administered to the rat. After 2 hours, the animals were euthanized and their tissues removed, weighed and counted for radioactivity. The total percentage of the dose in bone was calculated by assuming that the bone sample (femur) represents ⅕sth of the total weight of the skeletal system and distribution is uniform. The total blood dose was calculated by assuming that the blood comprises 6.5% of the total body weight. The total muscle dose was calculated by assuming that the muscle comprises 43% of the total body weight.

Biodistribution of $^{153}$Sm-PCTMP and $^{153}$Sm-BP2P

| Tissue or Organ | PCTMP | BP2P |
|---|---|---|
| Bone | 34.87 | 60.08 |
| Liver | 0.99 | 3.71 |
| Kidney | 1.42 | 1.21 |
| Spleen | 0.07 | 0.05 |
| Muscle | 4.77 | 1.53 |
| Blood | 6.27 | 0.87 |
| Heart | n/a | 0.07 |
| Lung | n/a | 0.17 |
| Brain | n/a | 0.01 |
| Stomach | n/a | 0.2 |
| Small Intestine | n/a | 0.39 |
| Large Intestine | n/a | 0.13 | n/a means not available as none was detected

For analysis of the bone fluorescence, two rats were injected with Tb-PCTMP or Tb-BP2P. After two hours of equilibration, the animals were euthanized and the femurs were removed.

For the fluorescence measurements, the instrument in FIG. 5 was modified. External illumination is directed from a UV source (curing lamp) fitted with a 270 nm bandpass filter through a flexible liquid light guide to the sample. A 550 nm bandpass filter was placed between the microscope objective (3) and the CCD (5) to select fluorescence and block background light. The collected images were converted to a TIFF format and were processed. Several line pairs of various frequencies were sampled and their modulation values were plotted as a function of line frequency. The AIM plots for the three endoscopes tested indicated that the limiting resolution is approximately equal for the three scopes. Resolution is dependent upon the mode or method used to display or view the image.

Figure 8A:
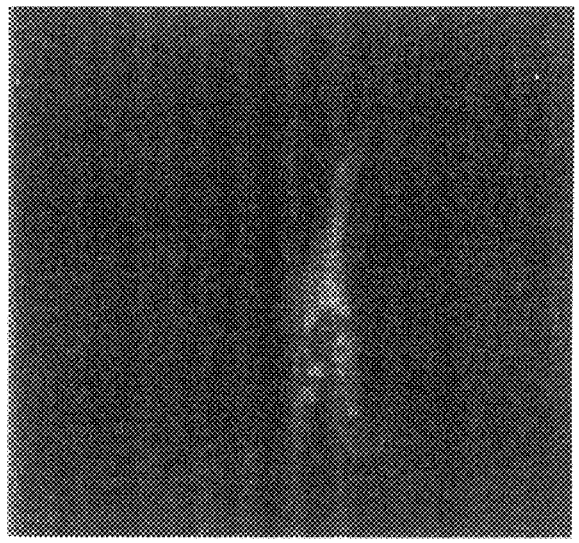
FIG. 8, a photograph, is the excised rat bone image of the femur using the micro-endoscope of FIG. 5 and shows the actual fluorescence image using monochromatic excitation and filtered emission and the false color contour plot. Color contours are: green-yellow=background signal; blue-purple=1.54×10$^{-15}$ moles Tb-PCTMP/pixel; red=3.35×10$^-$ 15 moles Tb-PCTMP/pixel.
Figure 8B:
Figure 9A:
FIG. 9, a photograph, is the white light, reflectance endoscopic image of the same rat femur of FIG. 8.
Figure 9B:

Upon visual inspection of the high resolution video monitor (7), resolution of 181 LP/mm can be obtained. Resolution of this magnitude allows objects spaced 2.76 $\mu$m apart to be resolved. Such magnification would allow analysis of subcellular organelles such as a nucleus (5–6 $\mu$m) or endoplasmic reticulum (3 $\mu$m). After electronic fidelity degradation, a resolution of 112 LP/mm is obtained which corresponds to a resolving power of 4.46 $\mu$m. The fluorescence image and false color image of FIG. 8 demonstrate this capability. White light corresponding images are presented in FIG. 9. Calibration curves similar to that of Example II were used to estimate the amount of Tb-PCTMP solute present in an imaged region of the bone (surface). Optical sampling to about 6 $\mu$m when the excitation is at about 270 nm and emission is at about 550 nm, produces flupresence fluence of approximately 66%. As calculated in a manner similar to Example II, it is possible to estimate the quantity of solute within a particular imaged zone. By sampling the entire region a calculated value of about 5.19 picomoles of solute is present.

EXAMPLE IV

This system can view gross tissue morphology differences based on the binding characteristics of the chelate. It is known that the physiological conditions of normal and neoplastic tissue vary drastically [see R. K. Jain and G. R. Martin, Cancer Res. 54, 5670 (1994)]. Thus these present chelates with the system described are able to image and aid diagnostic techniques in vivo.

Tumors were induced in Sprague Dawley rats via injection of 1,2 dimethylhydrazine dihydrochloride and the subsequent feeding of a high fat, meat-based diet. Subjects that contained potential colon abnormalities were identified using a three step process. i) Rats that exhibited weight loss and feeding difficulties were set aside as potential candidates. ii) These animals were inspected for signs of rectal bleeding or blackened fecal pellets, often an indication of a significant abnormal growth. iii) Finally, using a 2.5 mm diameter, 3 meter long, flexible micro-endoscope, the large intestine of several animals was inspected under white-light endoscopic visualization to confirm the presence of an abnormal tissue mass. One animal with an observable lesion was anesthetized, allowing it to respire during lavage introduction of the fluorescent marker. An aqueous solution of Tb-PTCMB at a concentration of 0.1 mmol/kg animal body weight, was administered to a Sprague Dawley rat using the 1.0 mm working lumen of the micro-endoscope. Introduction of the marker solution was made at the site of the suspect tissue mass with a volume necessary to fill the entire large intestine (method described in U.S. Pat. No. 5,456,245). The marker solution was allowed to reside in the large intestine for 20 minutes before sacrificing and dissecting the rat.

Upon dissection of the large intestine, a large occlusive mass approximately 4.5 cm by 5.0 cm was found approximately 15 cm from the rectum. Normal tissue was collected from the intestine about 10 cm removed from the suspect mass. Tissue samples from the mass and from the normal region of the intestine were then placed in saline and immediately transported for further histological preparation. Four frozen sections were prepared of all samples. Four slides from each tissue region were first left unstained for fluorescence microscopy imaging as described below and then stained with Hematoxylin and Eosin (H&E stain).

Figure 10A:
FIG. 10A, a photograph, is a standard microscopic image of H&E stained tissue taken from a site in the colon removed from the suspect mass and histologically judged to be normal.
Figure 11A:
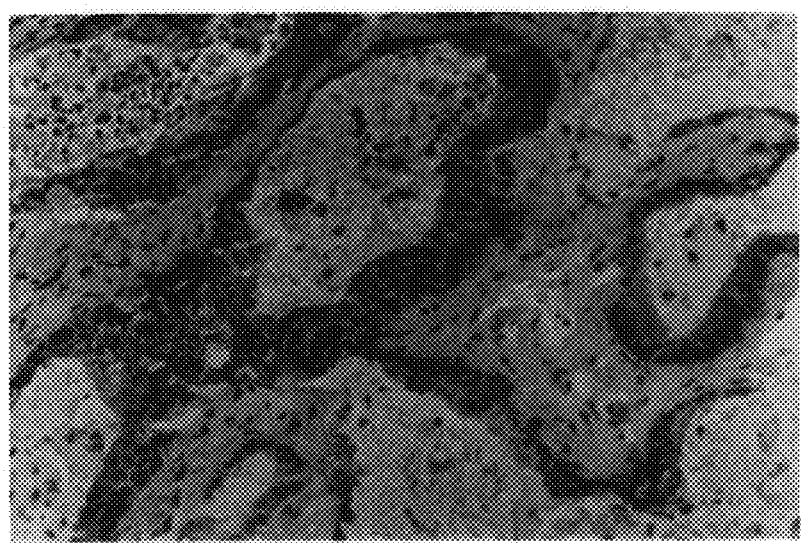
FIG. 11A, a photograph, is a standard microscopic image of H&E stained tissue taken from a site in the colon removed from the suspect mass and histologically judged to be adenocarcinoma.

Using standard histological criteria for diagnosis, tissue taken from the suspect site was determined to be adenocarcinoma. [See S. S. Sternberg Ed. "Histology of the Colon" in *Histology for Pathologists* (Raven Press, 1992); W. M. Copenhaven et al., "Histology of the Intestine" in *Bailey's Textbook of Histology* (The Williams & Wilkins Co. Baltimore, Mass., 17$^{th}$ Ed 1978) Chap. 16, pp 495–509; K. M. Pozharisski, "Tumors of the Intestines", *In Pathology of tumors in Laboratory Animals*, E, V. Turosov Ed. (IARC, Lyon) 1, 119–140 (1973)]. The tissue taken from a location removed from the abnormality was determined to be normal. Microscopic images of the regions in question, stained using H&E methodology, are shown in FIGS. 10A and 11A.

Figure 10B:
FIG. 10B, a photograph, is a white light reflectance microscopic image of unstained, Tb-PTCMB dosed tissue taken from a site in the colon removed from the suspect mass (normal).
Figure 10C:
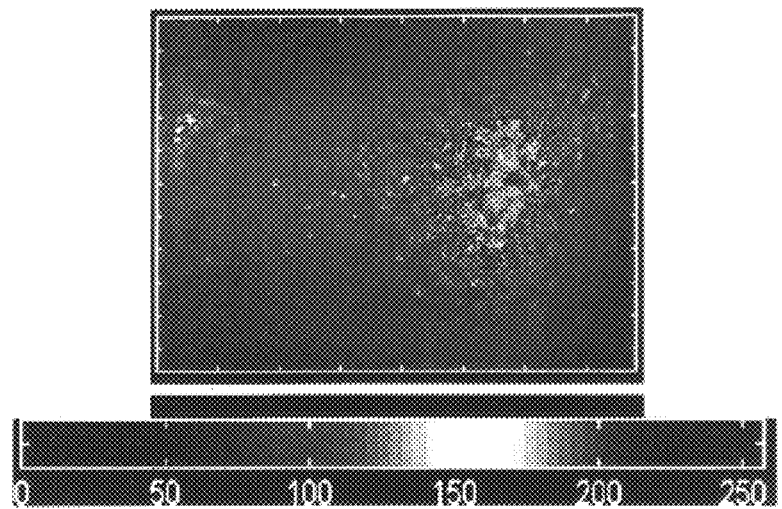
FIG. 10C, is a color contour enhanced, fluorescence microscopic image of unstained, Tb-PTCMB dosed tissue microscopic image of H&E stained tissue taken from a site in the colon removed from the suspect mass (normal).
Figure 11B:
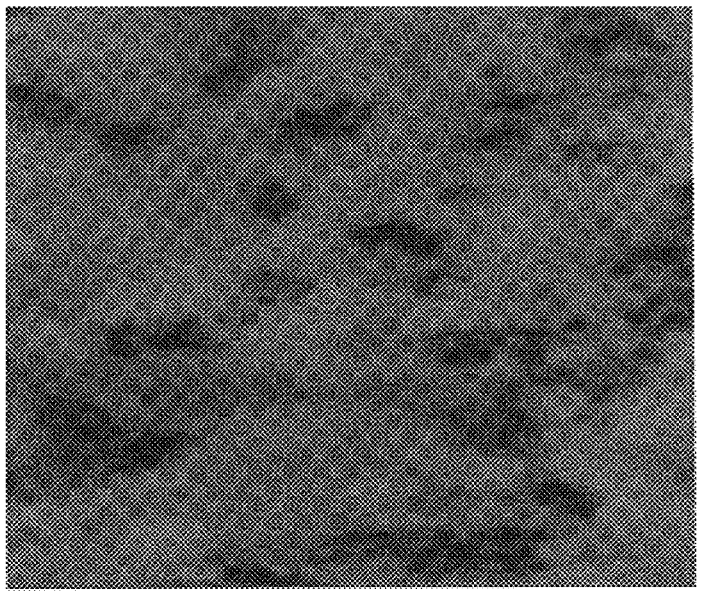
FIG. 11B, a photograph, is a white light reflectance microscopic image of unstained, Tb-PTCMB dosed tissue taken the suspect colon mass (adenocarcinoma).
Figure 11C:
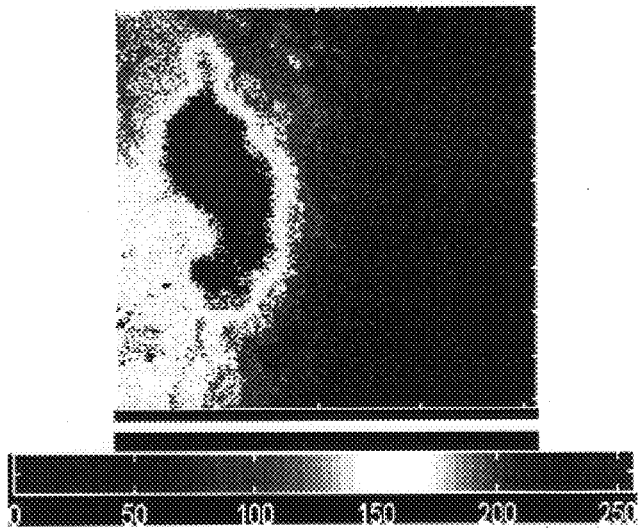
FIG. 11C, is a color contour enhanced, fluorescence microscopic image of unstained, Tb-PTCMB dosed tissue taken from a site in the colon mass (adenocarcinoma).

Using an in-house modified microscope, samples from the suspect and remote regions of the animal were imaged. The white-light reflectance images for the suspect region and that of the remote colon section are shown in FIGS. 10B and 11B. Shown in FIGS. 10C and 11C are the fluorescence images of the identical regions of the same tissues. As discussed above, these regions were subsequently stained with H&E for histological evaluation. False color contours in the fluorescence image correspond to the emission intensity and represent the relative amount of marker entrained in the tissue. A significant difference in solute uptake is indicated by the large difference in fluorescence intensity for normal versus neoplastic tissue. Chelate uptake accounts for the fluorescence signal detected in the normal tissue (FIG. 10C). Yet, based on the signal intensity, the relative difference between the quantity of marker solute found in the tissues is estimated to be an order of magnitude. While not absolutely conclusive evidence, the observed difference in fluorescent signal is significant enough to suggest some preferential or enhanced uptake of Tb-PTCMB by abnormal colon tissue. Such a significant relative difference would allow for the enhancement of contrast for cancers of the colon and thus, improved detection. Since this preferential marker uptake occurs during a low concentration, aqueous lavage through an endoscope working lumen, it could be possible to apply such a technique for contrast enhancement during colonoscopy using a sigmoidoscope modified for fluorescence imaging.

EXAMPLE V

HT-29 cell lines were obtained from American Type Culture Collection (ATCC) and maintained in Dulbecco's Modified Eagle Medium (DMEM) with 10% fetal bovine serum. Tree days prior to confluence, the cells were inoculated with 2 mL of 2 mM Tb-PCTMB and allowed to grow to confluence. Two days prior to confluence, the unbound TB-PCTMB was removed with four washings of PBS and the cells were removed from the flask with 3 mL of trypsin. The cell suspension was transferred to a centrifuge tube with 12 mL of growth media and spun a 1000 g for 10 minutes to pellet the cells. The media and the trypsin were removed and the cell suspension was resuspended in 5 mL of media. For ease in counting, 100 μL of the cell suspension was mixed with 100 μL of media in a microfuge tube. Fifty μL of this dilution was mixed with 50 μL of Trypan blue stain and loaded into the hemocytometer. The cells in 5 squares on the hemocytometer were counted where stained cells were dead and unstained cells were alive. Multiplication of the average count per square by the dilution factor (4) gave the number of cells×10$^4$ per mL. The number of cells reported is the average of three individual counts.

| Cytotoxicity Results HT-29 Cells | |
|---|---|
| Control | Tb-PCTMB Inoculated |
| Total Cell Population*: | Total (Cells/ml)*: |
| 5.30 × 10$^6$ | 4.70 × 10$^6$ |
| Live Cells: 94.3% | Live Cells: 91.5% |
| Dead Cells: 5.7% | Dead Cells: 8.5% |

*Average of triplicate counting.

The counting for the data in the above tables has been estimated as log K=19 by M. P. Hubbard and D. J. Bornhop in 1995. The value compares well with similar compounds as found by W. P. Cahceris et al., *Inorg. Chem.* 26, 958–960 (1987) and S. Aime et al., *J. Chem. Soc., Chem. Commun.* 1885–1886 (1966). The carboxylate analogs of the present chelates of Formula I show a thermodynamic stability constant of log K=19.5.

UMR106 cells were obtained from American Type Culture Collection and maintained in Basal Eagle Media with 10% fetal bovine serum. Cells were propagated so that 3×10$^7$ cells were contained in 25 mL. One day prior to confluence, the cells were inoculated with 2 mL of 2×10$^{-3}$ M Tb-PCTMP. At confluence, the media and Tb-TCTMP was removed with four washings of PBS. Cells were separated from the flask with 3 mL of trypsin, transferred to a centrifuge tube with 12 mL of media and spun at 1000 g for 10 minutes to pellet the cells. The pellet was resuspended in 2 mL of media and frozen by submersion of the tube into liquid nitrogen. The frozen mixture was scooped out of the tube and transferred to a mortar. To the mixture, an equal weight of sea sand and 10 mL of liquid nitrogen were added. This mixture was ground with a pestle for 30 minutes until liquefied. The resulting mixture was transferred to a centrifuge tube and spun at 10,000 rpm for 15 minutes leaving intact cells, sand and membranes in the pellet and the cytoplasmic organelles in the supernatant. The supernatant was spun at 45,000 rpm for 90 minutes in an ultracentrifuge tube to pellet the organelles. The membrane, cells and sand mixture was filtered through a course filter to remove the sand and a 10 μm filter to remove the intact cells. [This differential centrifugation is described by H. Pertoft and T. C. Laurent in *Methods of Cell Separations*, N. Castimpoolas, Ed. (C. Plenum Press, NY, 1$^{st}$ Ed. 1977) Chapt. 7.] Both the membranes and the organelles were smeared onto microscope slides and analyzed using a Zeiss microscope, modified for UV excitation. The organelle smear from the control slides exhibits no discernible fluorescence, while significant fluorescence was detected in the smear of dosed cells. No signal was detected in the membrane smears of either the control or the dosed cells.

| Cytotoxicity Results IEC-6 Cells | |
|---|---|
| Control | Tb-PCTMB Inoculated |
| Total Cells*: 5.70 × 10$^6$ | Total Cells*: 5.30 × 10$^6$ |
| Live Cells: 89.5% | Live Cells: 90.6% |
| Dead Cells: 10.5% | Dead Cells: 9.4% |

*Average of triplicate counting. Procedure detailed in Ref. 27

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for the diagnosis of a disease state in an animal which comprises administering to said animal an effective amount of a formulation comprising a complex having a compound of Formula (I)

(I)

wherein:

Z is (E) or T (F)

Y is (A), (B), (C), or (D)

T is —CH$_2$—COOH, $$-CH_2-\underset{OR}{\underset{|}{\overset{O}{\overset{\|}{P}}}}-OH; \quad (G)$$

(H), or (J)

where: R is H, C$_1$–C$_4$ alkyl or —CH$_2$CF$_3$;

R$^2$ is a NO$_2$, NH$_2$, isothiocyanato, semicarbazido, thiosemicarbazido, maleimido, bromoacetamido or carboxyl group;

with the proviso that Z is only (F) when (D) is present and Z is only (E) when (A), (B) or (C) is present;

with the proviso that when T is (H) or (J), then only one (H) or (J) may be present;

complexed with a metal ion of terbium (Tb), europium (Eu) or dysprosium (Dy); or pharmaceutically-acceptable salts thereof;

detecting the emission for fluorescence from said formulation, obtaining a fluorescent image; and analyzing the image for the diagnosis of the disease state.

2. The method of claim 1 where the formulation is administered as an injectable solution or as a wash solution.

3. The method of claim 2 wherein the dose of the complex is from about 0.001 to about 0.2 mmol/kg.

4. The method of claim 1 where the image is obtained using an endoscopic fluorescence imaging microscope.

5. The method of claim 4 where the image is obtained using a UV light source.

6. The method of claim 1 where a quantitative amount of the complex in the formulation is determined in a tissue imaged in vivo.

* * * * *

UNITED STATES PATENT AND TRADEMARK OFFICE
CERTIFICATE OF CORRECTION

PATENT NO. : 5,928,627  
DATED : July 27, 1999  
INVENTOR(S) : Garry E. Kiefer and Darryl J. Bornhop It is certified that error appears in the above-identified patent and that said Letters Patent is hereby corrected as shown below:

Column 4,  
Line 10, replace

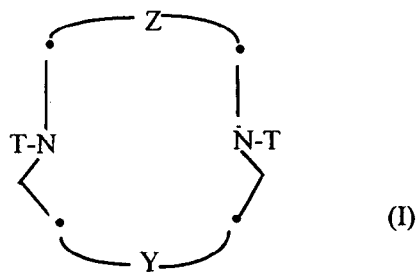

with

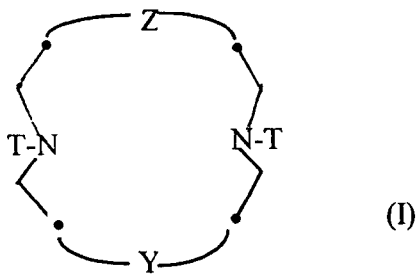

Column 27,  
Line 10, replace

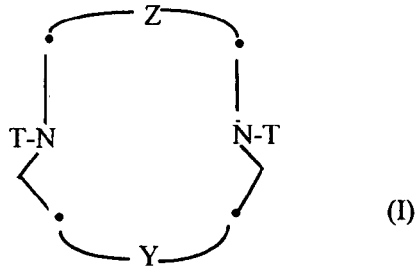

with

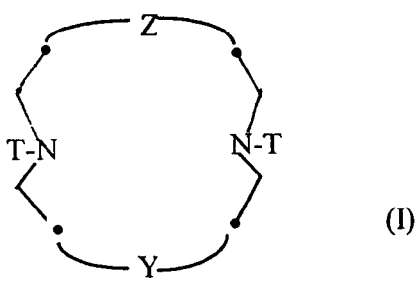

UNITED STATES PATENT AND TRADEMARK OFFICE
CERTIFICATE OF CORRECTION

PATENT NO. : 5,928,627
DATED : July 27, 1999
INVENTOR(S) : Garry E. Kiefer and Darryl J. Bornhop It is certified that error appears in the above-identified patent and that said Letters Patent is hereby corrected as shown below:

Column 9,
Scheme 2, last formula, replace

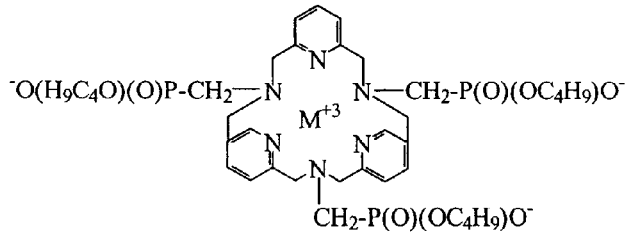

with

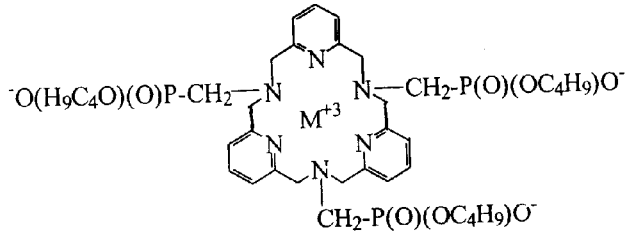

Signed and Sealed this

Twenty-fifth Day of June, 2002

Attest:

JAMES E. ROGAN
Attesting Officer   Director of the United States Patent and Trademark Office